United States Patent
Ruggiero (10) Patent No.: US 10,837,194 B2
(45) Date of Patent: Nov. 17, 2020

(54) PORTABLE RELAXATION POD

(71) Applicant: Inner Mission, LLC, Phoenix, AZ (US)

(72) Inventor: Annemarie Ruggiero, Phoenix, AZ (US)

(73) Assignee: Inner Mission, LLC, Phoenix, AZ (US)

( * ) Notice: Subject to any disclaimer, the term of this patent is extended or adjusted under 35 U.S.C. 154(b) by 0 days.

(21) Appl. No.: 16/828,304

(22) Filed: Mar. 24, 2020

(65) Prior Publication Data

US 2020/0318376 A1 Oct. 8, 2020

Related U.S. Application Data

(60) Provisional application No. 62/830,728, filed on Apr. 8, 2019.

(51) Int. Cl.
| | | |
|---|---|---|
| E04H 15/12 | (2006.01) | |
| A47C 7/66 | (2006.01) | |
| A61M 21/00 | (2006.01) | |
| E04B 1/82 | (2006.01) | |
| E04H 15/02 | (2006.01) | |
| E04H 1/12 | (2006.01) | |
| A61M 21/02 | (2006.01) | |

(52) U.S. Cl.
CPC .............. *E04H 15/02* (2013.01); *A61M 21/02* (2013.01); *E04H 1/12* (2013.01); *A47C 7/666* (2018.08); *A61H 2201/0134* (2013.01); *A61H 2201/0149* (2013.01); *A61H 2201/0169* (2013.01); *A61H 2205/12* (2013.01); *A61M 21/0094* (2013.01); *E04B 1/8218* (2013.01)

(58) Field of Classification Search
CPC ......... E04H 15/02; E04H 1/12; E04B 1/8218; A61M 21/0094; A47C 7/666
USPC .......... 135/96, 900, 902; 297/184.14, 184.15
See application file for complete search history.

(56) References Cited

U.S. PATENT DOCUMENTS

| | | | | |
|---|---|---|---|---|
| 1,710,675 A | * | 4/1929 | Lilleso-Petersen | A45F 4/04 135/96 |
| 2,050,492 A | * | 8/1936 | Lassiter | A47C 7/66 297/184.14 |
| 2,188,213 A | * | 1/1940 | Jo Wilson | E04H 1/12 135/95 |
| 3,498,587 A | * | 3/1970 | Friedberg | E04H 1/12 52/71 |

(Continued)

FOREIGN PATENT DOCUMENTS

| | | | |
|---|---|---|---|
| CN | 210018564 U | * | 3/2019 |
| CN | 209073844 U | * | 7/2019 |

(Continued)

*Primary Examiner* — Robert Canfield
(74) *Attorney, Agent, or Firm* — Burch & Cracchiolo, P.A.

(57) ABSTRACT

Portable relaxation pod. The portable relaxation pod includes a foldable exterior housing with walls, front flaps configured to close at least partially and an interior ceiling. Interior panels have acoustic foam and corrugated plastic layers. The interior panels abut the ceiling and walls. The portable seating system of a foldable chair equipped with a massage cushion is placed inside the exterior housing. A relaxation system includes an eye mask, headphones connected to an audio player and a portable foot massager, which is placed outside of the exterior housing in front of the seating system.

17 Claims, 10 Drawing Sheets

(56) References Cited

U.S. PATENT DOCUMENTS

| | | | | |
|---|---|---|---|---|
| 3,547,136 A * | 12/1970 | Koenig | | E04H 9/14 135/156 |
| 3,762,767 A * | 10/1973 | Powell | | A47C 15/00 297/217.5 |
| 3,799,608 A * | 3/1974 | Smutny | | E04H 15/001 297/184.14 |
| 4,826,245 A * | 5/1989 | Entratter | | A47C 7/72 297/217.5 |
| 4,926,893 A * | 5/1990 | Klopfenstein | | E04H 15/001 135/116 |
| 5,123,874 A * | 6/1992 | White, III | | E04B 1/34321 181/290 |
| 5,171,059 A * | 12/1992 | Patrick | | A47C 7/666 297/184.14 |
| 6,354,044 B1 * | 3/2002 | Lagace, Jr. | | A47C 7/72 297/184.14 |
| 8,690,239 B2 * | 4/2014 | Ishikawa | | A61H 23/02 297/217.1 |
| 10,737,054 B1 * | 8/2020 | Lynn | | A61M 21/02 |
| 2005/0113723 A1 * | 5/2005 | Ueyama | | G16H 50/20 601/15 |
| 2006/0283493 A1 * | 12/2006 | Charles | | E04H 1/1266 135/121 |
| 2008/0011345 A1 * | 1/2008 | Mohns | | A47C 7/666 135/88.01 |
| 2009/0039685 A1 * | 2/2009 | Zernov | | E04H 15/003 297/16.2 |
| 2010/0264789 A1 * | 10/2010 | Ton | | A47C 1/04 312/228 |
| 2013/0074894 A1 * | 3/2013 | Cook | | E04H 15/44 135/96 |
| 2013/0152987 A1 * | 6/2013 | Nelson | | E04H 15/32 135/96 |
| 2016/0008568 A1 * | 1/2016 | Attia | | A61B 5/486 600/28 |
| 2018/0223559 A1 * | 8/2018 | Lim | | E04H 15/64 |
| 2018/0320394 A1 * | 11/2018 | Reaves | | E04H 1/14 |

FOREIGN PATENT DOCUMENTS

| | | | | |
|---|---|---|---|---|
| GB | 2520971 A | * | 6/2015 | E04H 15/30 |
| JP | 11081723 A | * | 3/1999 | |
| JP | 2001112834 A | * | 4/2001 | |
| JP | 2001333991 A | * | 12/2001 | |

\* cited by examiner

FIG. 10

PORTABLE RELAXATION POD

FIELD OF THE INVENTION

The current invention relates to portable relaxation pods and methods for assembling and using the same.

BACKGROUND OF THE INVENTION

Individuals are stressed in their daily lives and seek ways to relax and relieve stress including use of massage chairs.

BRIEF SUMMARY OF THE INVENTION

A portable relaxation pod according to an embodiment of the present invention may provide a portable housing, the portable housing being foldable and comprising an exterior housing with walls, front flaps, an interior ceiling and interior panels abutting the interior ceiling and an interior surface of the walls, the interior panels each comprising an acoustic foam layer and a corrugated plastic layer, the front flaps being configured to close part way to accommodate a user; a portable seating system, the seating system being placed inside the exterior housing and comprising a foldable chair equipped with a massage cushion placed against a back surface and seat of the foldable chair; and a relaxation system, the relaxation system comprising an eye mask, headphones connected to an audio player and a portable foot massager located outside of the housing.

In another embodiment, the portable relaxation system may include a carrying system comprising a bag and cushioning member attached to at least one leg of the chair.

BRIEF DESCRIPTION OF THE DRAWINGS

Illustrative and presently preferred exemplary embodiments of the invention are shown in the drawings in which:

FIG. 4 is a view of components of the exterior housing of the present invention in which (A) shows corrugated plastic layer, (B) shows interior side and rear panels; (C) shows a cross-section of interior side and rear panels; and (D) shows and acoustic foam layer;

DETAILED DESCRIPTION OF THE INVENTION

The present invention comprises various embodiments of relaxation pod 10 and methods for assembling 100 and using 200 relaxation pod 10.

In the present invention, the inventor recognized that workers and employees on the job do not have access to privacy during work breaks and, as a result, breaks are not restorative. The same is also true of the public seeking a relaxing break, such as those passing through airports who may be encountering travel stress. Known methods and devices for providing relaxation in the short-term or otherwise have significant drawbacks as the inventor here recognized.

Relaxation pod 10 of the present invention creates a new device and method to assist in relaxation. Relaxation pod 10 is private but not claustrophobic; blocks light; is small in size; is durable and can accommodate people of different heights and weights; provides equipment that is clean and allows for frequent cleaning; is fully portable and can be carried by one person even in multiple-story buildings without elevator access. No known device incorporates all of these features in a single, portable device.

Prior art methods and devices for assisting in relaxation have significant drawbacks as the inventor recognized. Simply using a meditation app that can be accessed via the Internet or other aids downloaded on a smartphone or tablet do not provide privacy, involve only the auditory sense and require the user to have tremendous discipline and initiative to use the mediation app.

While self-contained relaxation environments exist as a separate room or separate temporary-type building, they are often for use with groups, which many users do not like. In addition, they require a significant capital outlay, are relatively permanent, large and heavy, with high costs of ongoing cleaning and maintenance. Moreover, using these self-contained relaxation environments may result in all-but permanent loss of space in the area occupied by such a self-contained relaxation unit. Finally, many users seeking a restorative break shy away from using such spaces because of the stigma associated with having others know they are under stress or being perceived as taking time off from work to "relax" instead of work. Relaxation pod 10 of the present invention solves these problems that the inventor recognized because it is private, can be used individually for a short period of time and does not result in loss of usable space because it can be easily assembled, disassembled and is fully portable.

Electric massage chairs and massage stations also have drawbacks. Electric massage chairs are often provided in noisy, public locations that do not permit the user to "tune out" other stimuli. In addition, they cannot be carried or otherwise easily moved in the absence of equipment. A massage chair with a massage therapist has still other problems. Many people do not like to be touched by another person. Moreover, these devices require the user lean face-down into a pillow, ruining styled hair and make-up. In addition, these devices and methods only involve the touch sensation, as opposed to the full sensory experience provided by relaxation pod 10.

Relaxation pod 10 overcomes these disadvantages and will now be described with reference to the drawing Figures.

Relaxation pod 10 comprises housing 12, seating system 14, relaxation system 16 and carrying system 17. FIGS. 1-3, 5.

Figure 1:
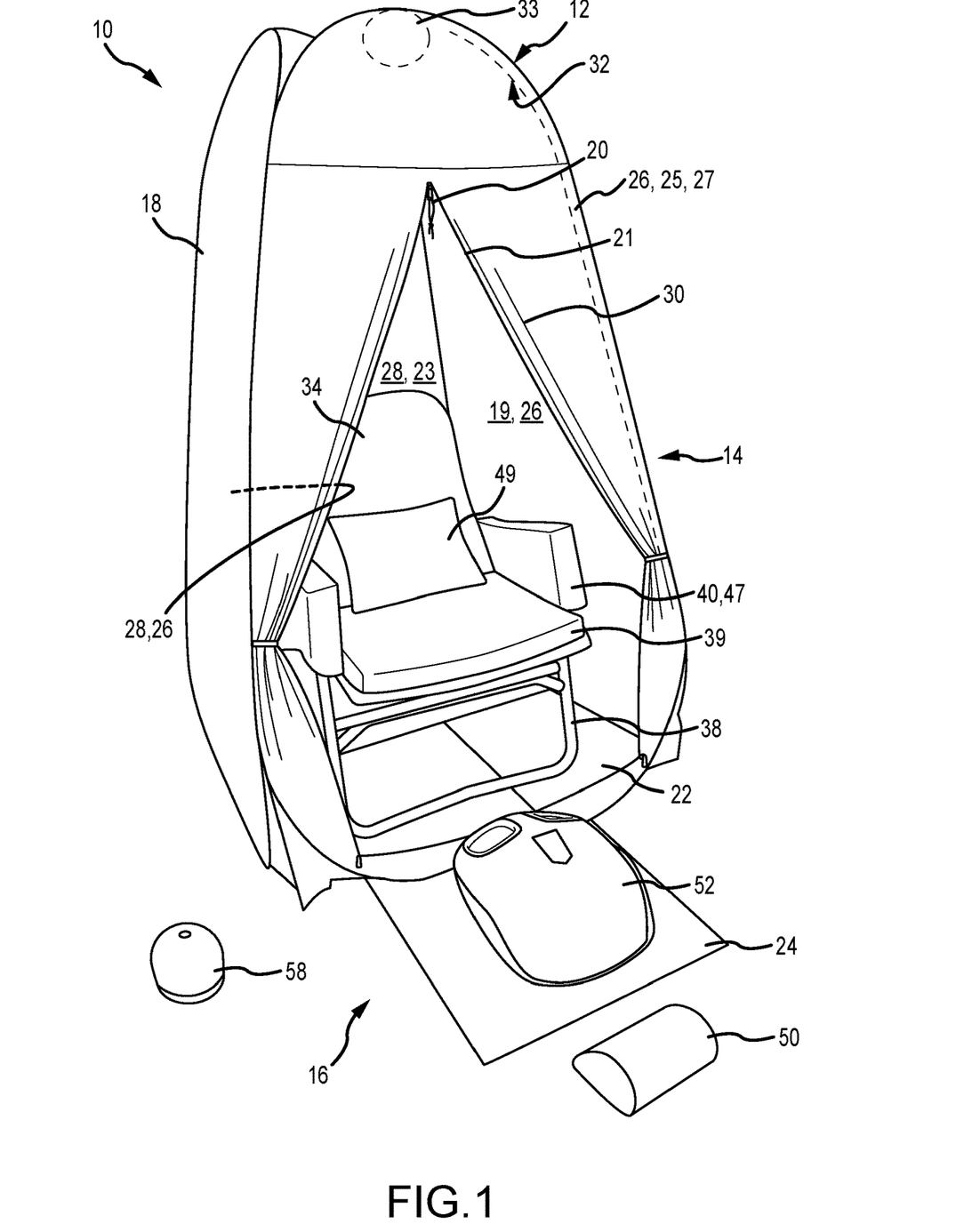
FIG. 1 is a view of an embodiment of a relaxation pod of the present invention.
Figure 2:
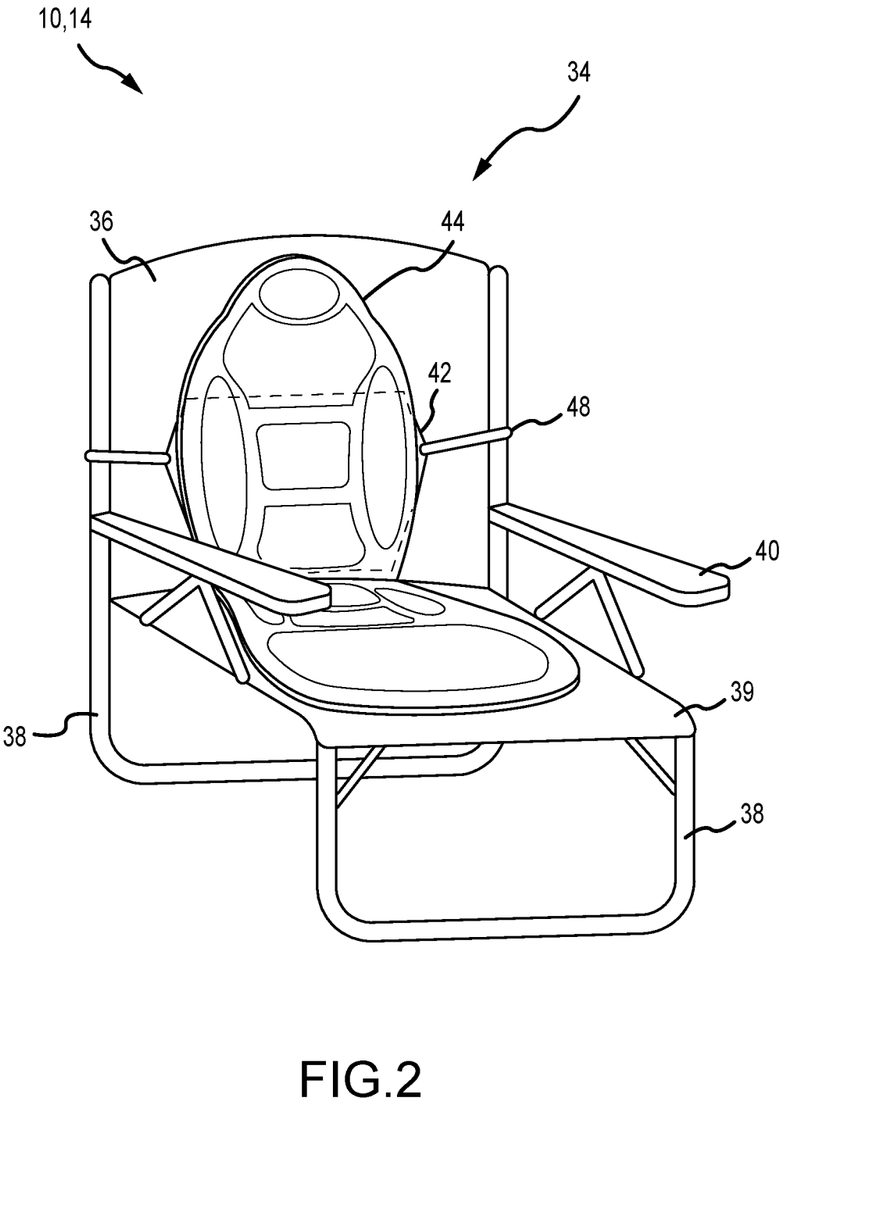
FIG. 2 is a view of an embodiment of the seating system of the present invention showing a chair with lumbar pillow and massage cushion.
Figure 3:
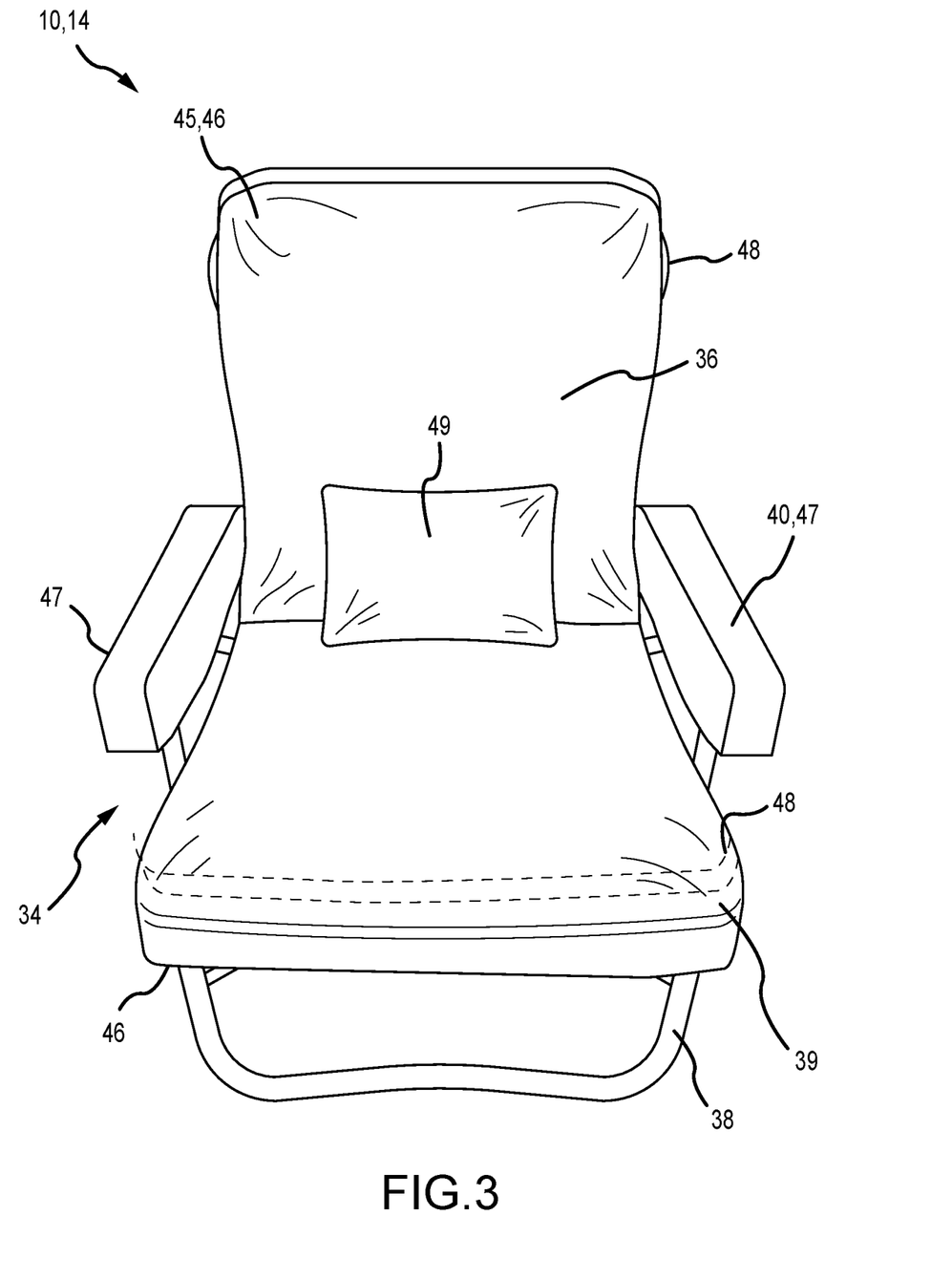
FIG. 3 is a view of an embodiment of the seating system of the present invention showing a chair with cover and neck pillow.
Figure 4A:
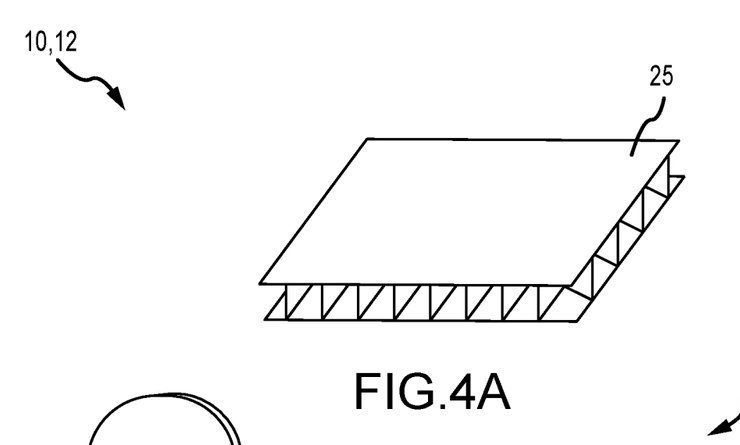
Figure 4B:
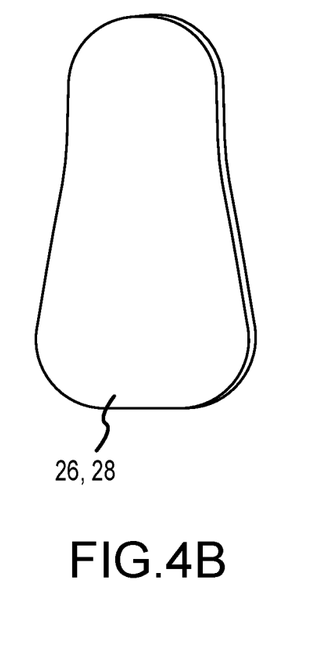
Figure 4C:
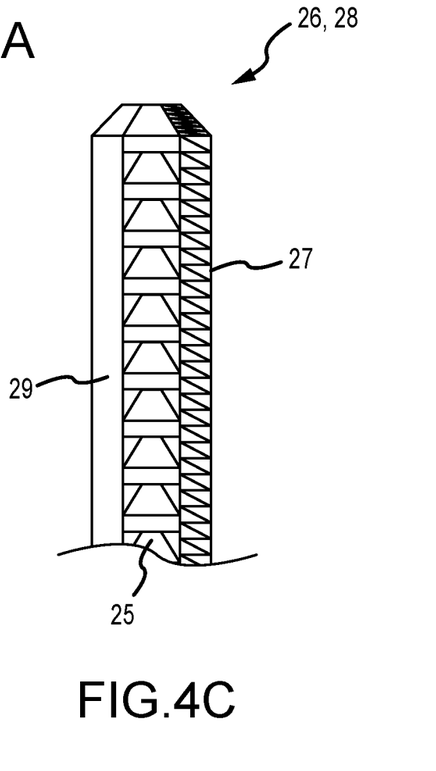
Figure 4D:
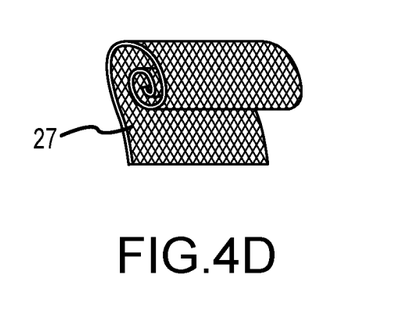

Seating system 14 comprises chair 34 and chair cover 46, as well as various cushions (e.g., massage cushion 44, top cushion 45) and pillows (e.g., lumbar pillow 42, neck pillow 49) described below. FIGS. 1-3. Chair 34 comprises back 36, legs 38, seat 39 and arms 40. Chair 34 is lightweight, portable and has a reclining feature that permits back 36 to recline. In the embodiment shown, chair 34 can support up to 400 pounds in weight. Further, in an embodiment, arms 40 and legs 38 are of aluminum tubular construction; however, other configurations and lightweight, durable metals could be used, so long as the chair remains lightweight and can support people of varying heights and weights. In an embodiment, chair 34 comprises a portable, reclining chair with two sets of U-shaped legs 38 of tubular construction in which seat 39 and back 36 comprise fabric stretched between tubular supports. FIG. 2.

As best seen in FIG. 2, lumbar pillow 42 is placed against back 36 of chair 34 just above seat 39 and secured with at least one flexible fastener, such as with straps 48. In the embodiment shown, straps 48 comprise hook-and-loop fastener straps. In another embodiment, lumbar pillow 42 may be attached to back 36 using other types of attachment means or flexible fasteners. As used herein, "flexible fastener" means any straps, ties, belts, bungee cords or any other fastener that is flexible and adjustable, including strips of leather, cloth, cord, fabric, plastic, rubber or other suitable materials with an attachment mechanism including buckles, hooks, snaps, hook-and-loop fasteners, hook-and-pile fasteners, loops, knots, rachet mechanisms and the like for holding an item substantially in place. Lumbar pillow 42 comprises known lumbar pillows that are commonly available; however, a custom lumbar pillow may also be used.

Massage cushion 44 comprises a commercially-available electric massage cushion with a variety of massage and heat options for the back, neck and seat area for user 70. In the embodiment shown, such options are shiatsu, vibration and rolling massage functions, as well as heat, although massage cushion 44 could be configured for any of these functionalities either separately or in combination and therefore should not be viewed as being limited in that respect. In seating system 14, massage cushion 44 is placed over lumbar cushion 42. FIG. 2. In another embodiment, massage cushion 44 could also be secured to chair 34 by straps or other attachment means. In yet another embodiment, massage cushion 44 could be of a custom design or could be integral to chair 34.

Figure 6:
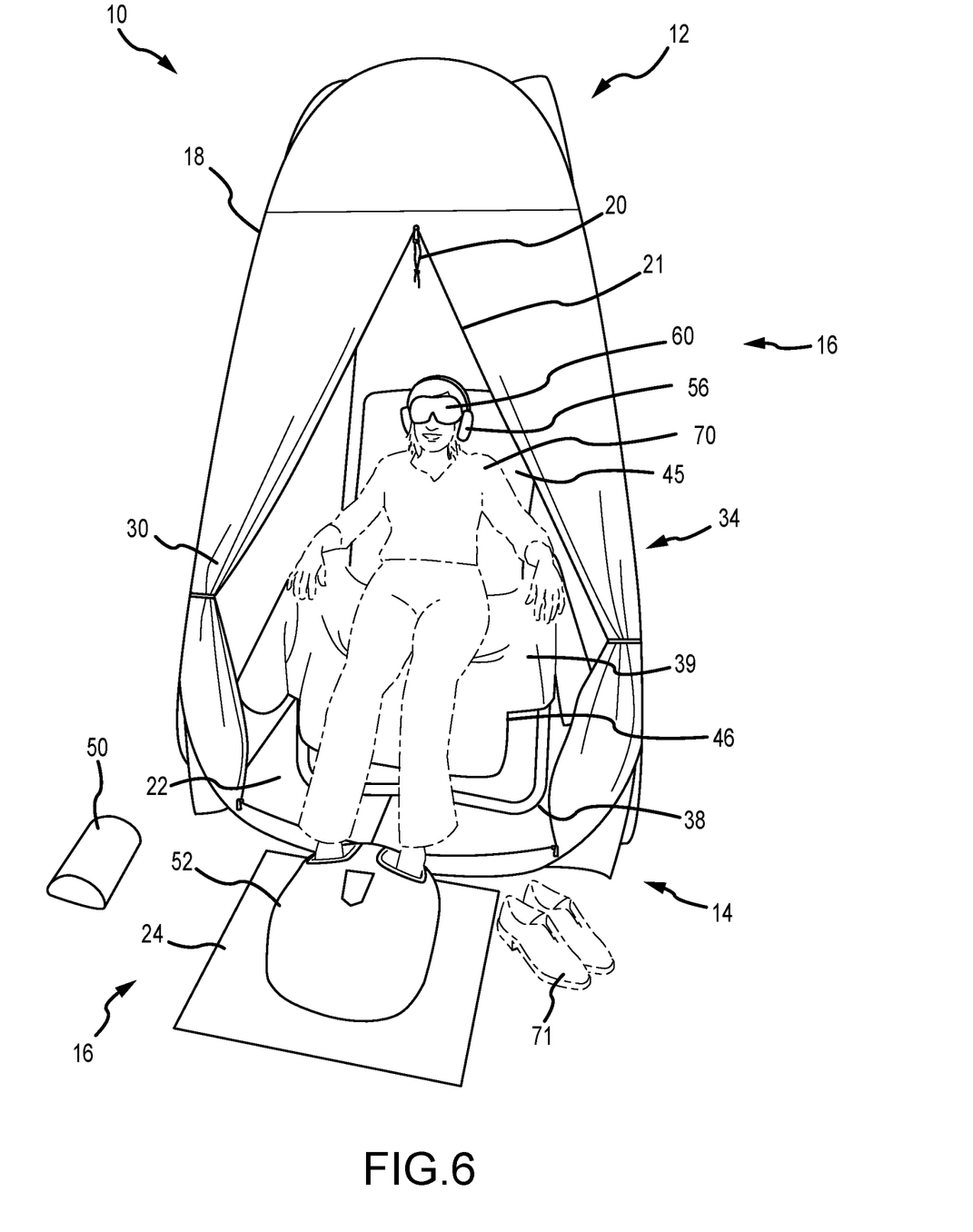
FIG. 6 is a front view of the relaxation pod of the present invention as occupied by a user.

Chair cover 46 is then placed over back 36, seat, 39 and arms 40. Chair cover 46 may comprise multiple covers designed to cover each chair component separately, as shown in the embodiment shown in FIG. 3. For example, as shown in an embodiment, arm covers 47 are separate from chair cover 46. FIG. 3. In another embodiment, chair cover 46 may be an integral cover configured to cover back 36, seat 30 and arms in a single cover. FIG. 6. In the embodiments shown, chair cover 46 comprises a soft-feel vinyl fabric that feels like a soft leather, but which may be cleaned with disinfectants without damaging the fabric.

Figure 5:
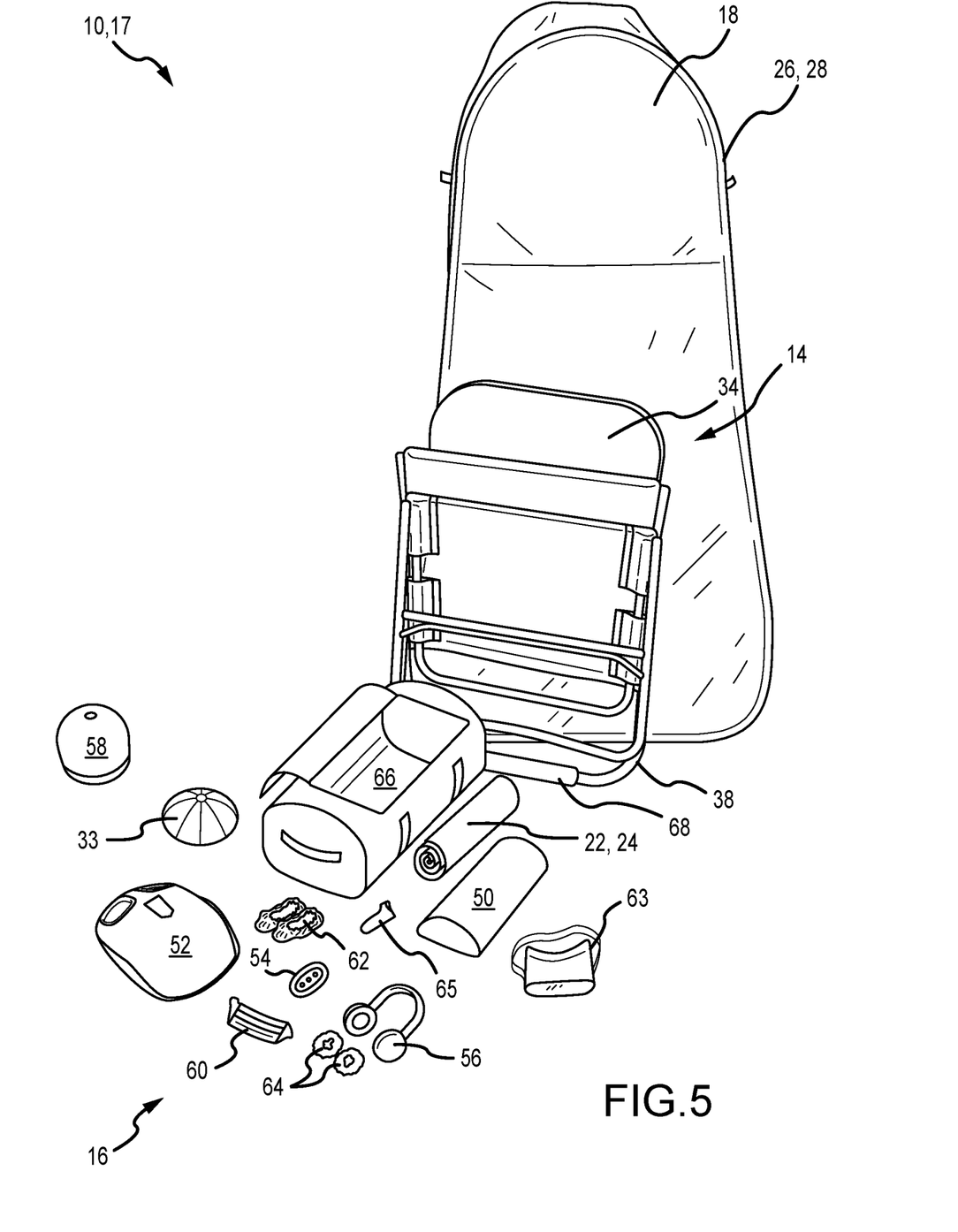
FIG. 5 is a view of an embodiment of a carrying system of the present invention showing the exterior housing, and folded chair of the present invention packed for transport chair, as well as a bag into which mats and components of the relaxation system may be packed.

Top cushion 45 is configured to be approximately the same size as back 36 and seat 39. Top cushion 45 may be placed over back 36, lumbar pillow 42, massage cushion 44 and chair cover 46, although other configurations are possible. FIGS. 2-3. In the embodiment shown, top cushion 45 is also covered in the same fabric as chair cover 46. Top cushion 45 is secured to chair 34 with straps 48 comprising hook-and-loop fasteners although other attachment means or flexible fasteners could be used as would be apparent to one of ordinary skill in the art after becoming familiar with the teachings of the present invention. FIG. 3. Neck pillow 49 is then placed on chair 34. FIGS. 1, 3. In the embodiment shown, top cushion 35 is configured to be folded with chair 34 when it is folded for packing as is explained in more detail below. FIGS. 3, 5. In the embodiments shown, seating system 14 is configured to be folded and carried, fully assembled in the manner described.

In another embodiment, chair 34 may be folded individually, with chair cover 46, as well as various cushions (e.g., massage cushion 44, top cushion 45) and pillows (e.g., lumbar pillow 42 neck pillow 49), being assembled on-site in the manner described above.

Although in embodiments described, chair 34 comprises a portable, folding, reclining, tubular chair with lumbar pillow 42, neck pillow 49, massage cushion 44, top cushion 45 and chair cover 46, other configurations are possible as would be apparent to one of ordinary skill in the art after becoming familiar with the teachings of the present invention. In another embodiment, many of the components of seating system 14 could be integral to chair 34, including lumbar pillow 42, massage cushion 44, neck pillow 49 and top cushion 45 and chair cover 46, so long as chair 34 remains lightweight, portable, durable, configured for people of different heights and weights, and capable of being folded or otherwise reduced in size for carrying. Thus, the invention should not be viewed as being limited in this respect.

As is explained in more detail below, to create relaxation pod 10, seating system 14 is placed inside housing 12, which will now be described with reference to the Figures. Housing 12 comprises exterior housing 18, interior and exterior floor mats 22, 24, interior side panels 26, interior rear panel 28, and light 33. FIG. 1.

Figure 7:
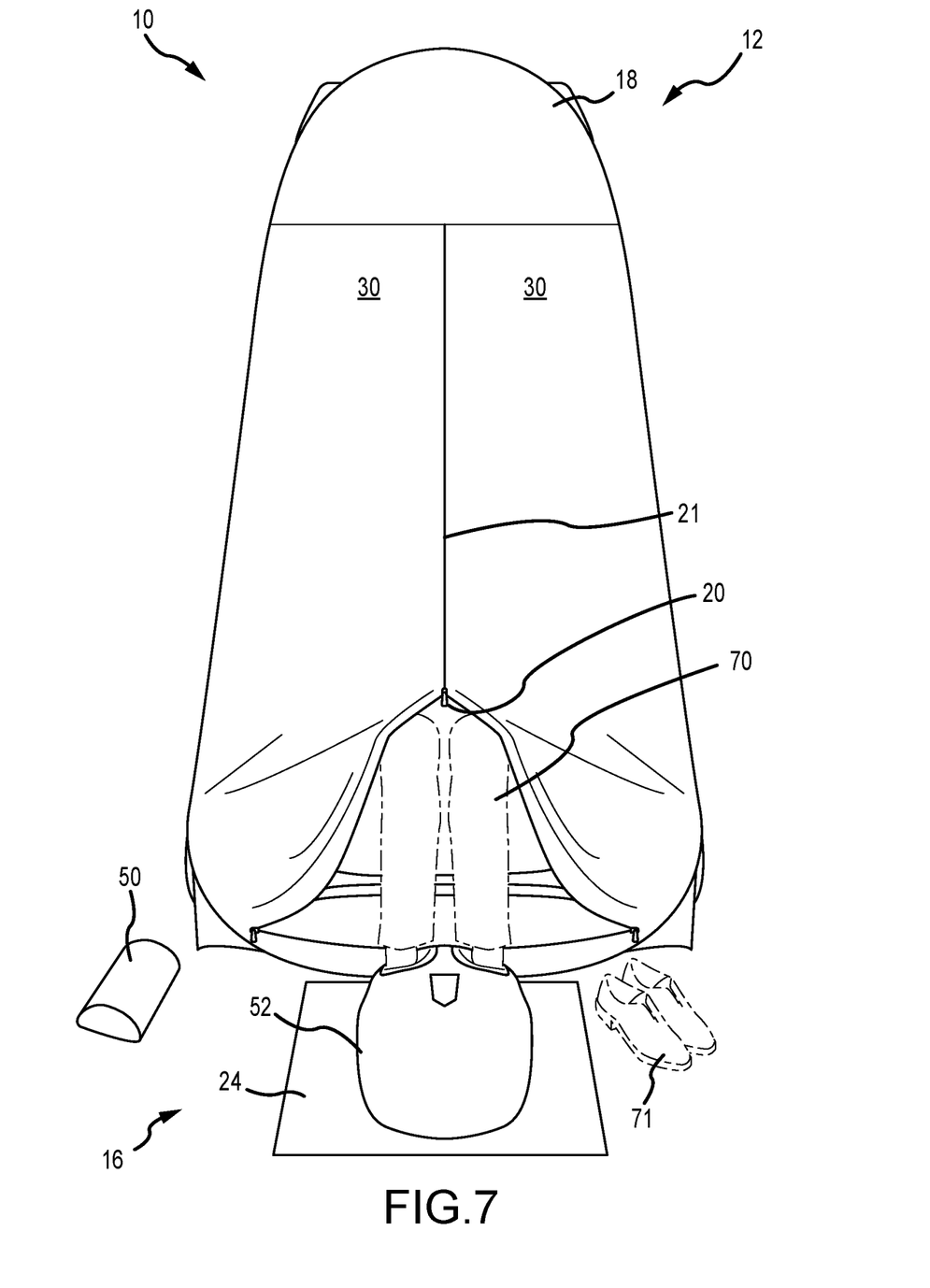
FIG. 7 is a front view of the relaxation pod of the present invention as occupied by a user with front flaps of the housing partially closed.

Exterior housing 18 may comprise a tent-like enclosure with front flaps 30, zippered closure 21 and zip cord 20; preferably, exterior housing 18 is sufficiently large to comfortably accommodate seating system 14 as occupied by user 70. FIGS. 1, 6, 7. Front flaps 30 are connected to a closure mechanism, which is shown in an embodiment as zippered closure 21, but the invention should not be viewed as being limited in this respect. Zip cord 20 attached to zippered closure 21 enables user 70 to close front flaps 30 while seated in seating system 14 inside exterior housing 18 with legs extending outside exterior housing 18, as is explained in additional detail below. Types of closure mechanisms other than zippers may be used for closing front flaps 30, such as snaps, hook-and-loop closures, as would be familiar to one of ordinary skill in the art after becoming familiar with the teachings of the present invention so long as they permit front flaps 30 to be closed part way and substantially block light when closed. In an embodiment shown, exterior housing 18 comprises dark colored walls 19, back 23 and ceiling 32 that block out light. In an embodiment shown, a modified pop-up tent was used; however, the invention should not be viewed as being limited in that respect.

Housing 12 further comprises interior floor mats 22 and exterior floor mat 24. In the embodiments shown, floor mats 22 were cut and sized to fit the floor contours of exterior housing 18. FIG. 1. Although shown in two pieces, the configuration of interior floor mats 22 should not be viewed as being limited in that respect, as floor mat 22 could comprise a single component or multiple component parts. Exterior floor mat 24 is configured to fit beneath foot massager 52. FIG. 1, 6, 7. In the embodiments shown, interior floor mats 22 and exterior floor mat 24 are configured to be rolled or folded to fit inside bag 66 of carrying system 17 and comprise mats made from polyvinylchloride (PVC) material, although rubber or another suitable material could also be used.

To create a sound-dampening environment, walls 19 of exterior housing 18 are lined with interior side panels 26 and interior rear panel 28 which are configured to match the interior dimensions and shape of walls 19 and back of exterior housing 18, respectively. FIGS. 1, 4. Interior side panels 26 are configured to abut walls 19 and ceiling 32 when placed inside exterior housing 18, while interior rear panel 28 is configured to abut back 23 and ceiling 32. As shown in FIG. 4, the removable interior panels 26, 28 comprise a layered construction of acoustic foam layer 27, corrugated plastic layer 25 and cover 29. Although interior panels, 26, 28 may be removable (although this is not required), interior panels 26, 28 are configured to be folded and unfolded and to remain inside exterior housing 18 while it is folded, unfolded, and transported. Thus, interior panels 26, 28 are also sufficiently rigid to stand substantially upright or erect when exterior housing 18 is stood-up or erected to an upright position.

In an embodiment shown in FIG. 4, acoustic foam layer 27 comprises an open-cell or "egg-crate" type polyurethane foam, although other similar materials may be used provided they are lightweight, sound-absorbing, capable of being cut to size, capable of being folded, and relatively thin to avoid taking up too much interior volume of housing 18. In addition, the material must be sufficiently rigid to enable it to stand upright inside housing 18, despite having been folded and unfolded. In the embodiments shown, interior panels 28, 30 were configured so that the acoustic foam layer 27 abuts walls 19 and back 23 of exterior housing 18 since acoustic foam layer 27 comprises a porous material, although the invention should not be viewed as being limited in that respect.

In an embodiment shown in FIG. 4, corrugated plastic layer 25 comprises fluted polypropylene sheet commercially available as Coroplast; however, other types of fluted polypropylene sheet or corrugated plastic sheet could be used provided that they are lightweight, provide some soundproofing, capable of being folded, capable of being cut to size, capable of being wiped down with chemical sanitizer and relatively thin to avoid taking up too much interior volume of exterior housing 18. In addition, as in the case of acoustic foam layer 27, the material must be sufficiently rigid to enable it to stand upright inside housing 18, despite having been folded and unfolded.

Cover 29 is placed over corrugated plastic layer 25. FIG. 4. Interior panels 26, 28 are placed inside exterior housing 18.

Housing 12 further comprises light 33. FIG. 1. In the embodiments shown, light 33 comprises an inflatable, battery-operated light attached to ceiling 32 of exterior housing 18 using hook-and-loop fastener straps 48, although other attachment means or types of straps could be used. Advantages of using this type of light are it is light-weight, safe for the user 70 sitting underneath of it should it become dislodged, provides light for maneuvering without disturbing user 70, and is sufficiently small to fit in bag 66 for transport. Light 33 may comprise other types of portable battery-operated lights with these same characteristics as would be familiar to one of ordinary skill in the art after becoming familiar with the teachings of the present invention.

Relaxation pod 10 further comprises relaxation system 16. An advantage of relaxation system 16 is that it provides user 70 with multiple sensory means for aiding in relaxation, including soothing sound, dark environment, foot massage, and soothing aroma, in addition to the massage and optional heat features provided by massage cushion 44. As shown in FIGS. 1, 5-7, relaxation system 16 comprises headphones 56 and audio player 54, scent diffuser 58, foot massager 52, eye mask 60, footrest 50, as well as earpiece covers 64 and foot covers 62. Other embodiments of the present invention may include some but not all of the aforementioned components.

In embodiments shown, headphones 56 comprise noise cancelling headphones in signal communication with audio player 54. The communication means may be wired or wireless depending on the communication configuration of audio player 54 which may be an MP3 player, smartphone, tablet or other similar device onto which appropriate audio meditation tracks, whether voice or music or both, have been downloaded. In the embodiment shown, audio player 54 may be provided as part of relaxation system 16; however, in another embodiment audio player 54 may also comprise user 70's own device onto which the tracks have been downloaded. Meditation tracks may also be streamed or downloaded. FIGS. 4, 6. In another embodiment, a meditation app may be used. Earpiece covers 64 may be used in the case of multiple users 70 in accordance with sound hygiene practices; however, this may not be necessary where relaxation pod 10 has one user 70, for example. In that case also, personal ear buds ore personal headphones may be used instead of headphones 56, as would be apparent to one of ordinary skill in the art after becoming familiar with the teachings of the present invention.

In embodiments shown, scent diffuser 58 comprises a waterless, battery-operated oil diffuser, which is preferred because it allows for portability, ease of set-up and allows user 70 to opt out of using this aroma therapy as it is easily removed from housing 12. FIG. 1. However, other types of scent diffusers may also be used.

Foot massager 52 comprises a commercially-available electronic portable foot massager. In embodiments shown, foot massager 52 is placed on top of exterior floor mat 24 to prevent foot massager 52 from slipping. Foot massager 52 is placed outside of housing 12 not only to allow for adjustment of leg position, but also to reduce noise sensed by user 70 from foot massager 52 and lessen feelings of claustrophobia. Foot covers 62 may be used in the case of multiple users 70 in accordance with sound hygiene practices; however, this may not be necessary where relaxation pod 10 has one user, for example. In an embodiment in which user 70 does not want to use foot massager 52, relaxation system 16 may comprise footrest 50. FIG. 1, 6, 7.

Relaxation system 16 comprises eye mask 60 to keep the environment in relaxation pod 10 dark for user 70. In the embodiments shown, eye mask 60 is disposable again in keeping with sound hygiene practices. In the embodiments shown, eye mask 60 comprises a disposable surgical mask. In an alternative embodiment, eye masks 60 personal to each user 70 could be used.

In another embodiment, relaxation system 16 may comprise an optional leg blanket (not shown). The blanket may be made of fleece or other suitable, washable material.

In another embodiment, relaxation system 16 may comprise a virtual reality system comprising virtual reality headset 63 and control 65. FIG. 5. Virtual reality headset 63 and 65 may be used separately or in combination with various of the other elements of relaxation system 16 of the present invention.

As would be familiar to one of ordinary skill in the art after becoming familiar with the teachings of the present invention, components of the relaxation system described above may be controlled individually or with a single control. In an embodiment, the single control may be a smart device equipped with an application for controlling some or all of the components of relaxation system 16 of the present invention. In addition, in an embodiment, functioning of the various components of relaxation system 16 may be automated.

In yet another embodiment, hygienic supplies may be dispensed automatically, such as in the case of an auto-disinfectant system that would spray disinfectant on the surfaces of the present invention after each user 70. In addition, the relaxation system 16 may include a locker for the user's 70 shoes 71 and other personal items.

Relaxation pod 10 further comprises carrying system 17. FIG. 5. Carrying system 17 comprises cushioning member 68 configured to attach to one or both legs 38 of chair 34. In the embodiment shown, cushioning member 68 comprises a pool noodle, cut to fit over chair leg 38, although other types of cushioning members are possible. FIG. 5. Cushioning member 68 is used to cushion the hands or shoulders of a person carrying seating system 14 via the legs 38 of chair 34, but is configured to be removable for setting up seating system 14. Carrying system 17 further comprises a carrier (e.g., bag 66) configured to hold all components of relaxation pod 10, except for exterior housing 18 (with interior panels 26, 28), and seating system 14. FIGS. 31, 32. In an embodiment, floor mats 22, 24 are sized to fit not only inside exterior housing 18, but also within bag 66 when rolled for packing and transport. In an embodiment, bag 66 may be made of water-resistant material to keep components of relaxation pod 10 dry in the event of rain. When seating system 14 and exterior housing 18 are folded and packed for transport and the remaining components are packed in bag 66, one person of average size can carry the entire relaxation pod 10. FIG. 5.

Thus, relaxation pod 10 of the present invention comprises a combination of elements having a synergistic effect that is greater than each of its individual elements. Relaxation pod 10 provides a system that is fully portable and can be carried by one person and is adjustable to accommodate individuals of widely varying sizes. In addition, since relaxation pod 10 is configured so that exterior housing 18 may be only partially closed with user's 70 feet outside of housing 12 in foot massager 52 during use, relaxation pod 10 can be used to synergistic effect in reducing noise for the user 70 (which is also aided by noise-cancelling headphones 56), as well as lessening feelings of claustrophobia that might arise from having the user 70 fully enclosed inside housing 12 during a meditation session. FIG. 7. This can be seen when relaxation pod 10 is described in conjunction with embodiments of methods 100, 200 for assembly and method 300 for use.

Figure 8:
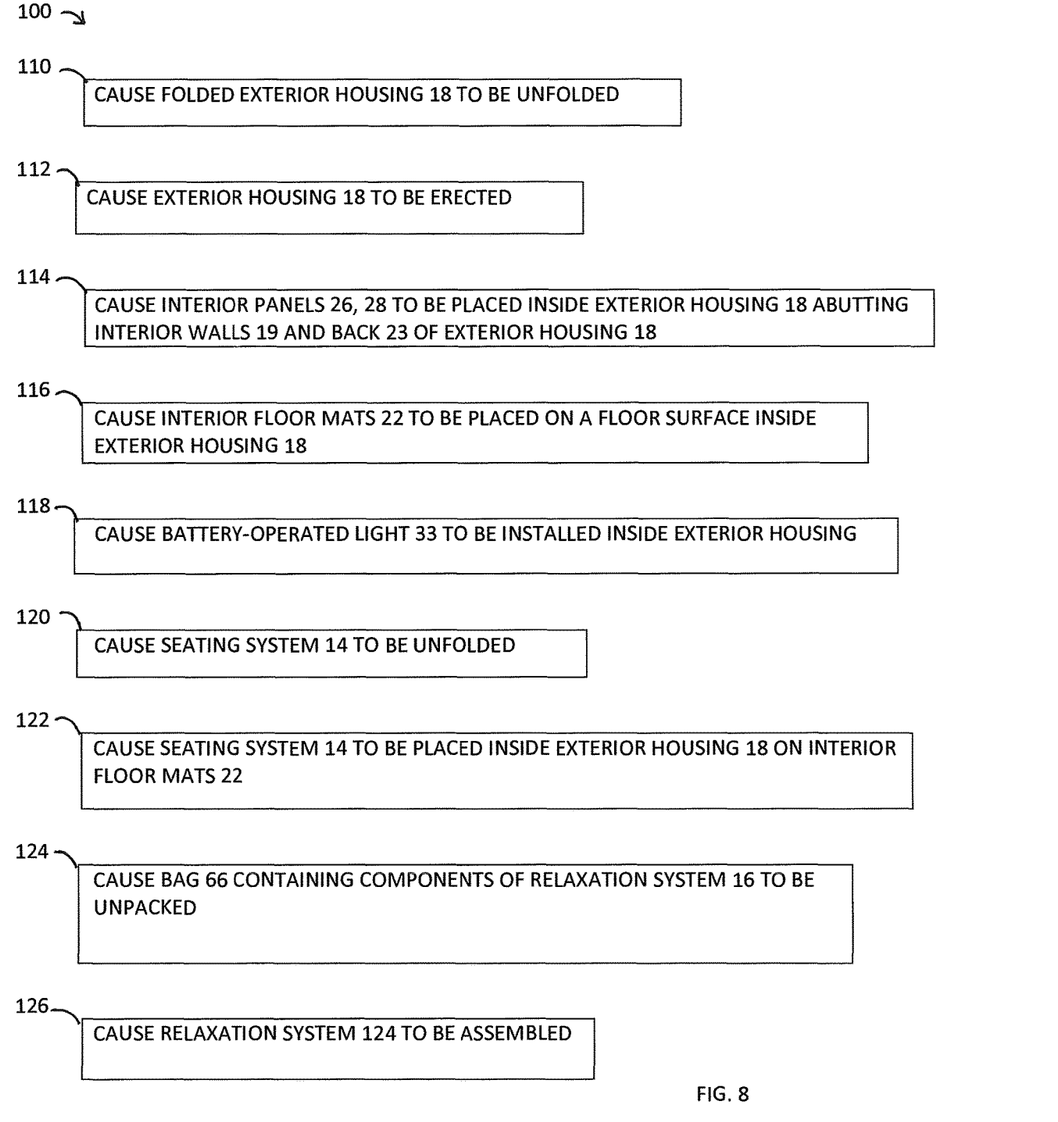
FIG. 8 illustrates steps in an embodiment of a method of the present invention for assembling the relaxation pod.

Method 100 of the present invention for assembling relaxation pod 10, will now be described with reference to FIG. 8.

At the outset, folded exterior housing 18 and interior panels 26, 28, folded seat assembly 14 and the remaining components (e.g., relaxation system 16 components and floor mats 22, 24) packed in bag 66 are transported to a desired location to assemble relaxation pod 10.

Folded exterior housing 18 including interior panels 26, 28 is unfolded 110 and unzipped. In step 114, interior panels 26, 28 are put in place, abutting walls 19, back 23 and ceiling 32. Exterior housing 18 is caused to be erected at step 112. Bag 66 is unpacked at step 124. Interior floor mats 22 are unrolled and caused 116 placed inside exterior housing 18 to cover the floor of exterior housing 18, although this is not required. Exterior floor mat 24 is unrolled and placed outside of exterior housing, making housing 12.

In the embodiments shown, light 33 is inflated and installed 118 inside exterior housing 18. In one embodiment, light 33 is attached to ceiling 32 using hook-and-loop fasteners, although other means are possible. Then light 33 is turned on.

Folded seating system 14 (fully assembled in the manner described above) is unfolded 120. Cushioning member 68 is removed from leg(s) 38 of chair 34. Seating system 14 placed 122 inside exterior housing 18 on interior floor mats 22.

Components of relaxation system 16 are organized and assembled 126. Massage cushion 44 is plugged in to an electrical outlet or otherwise connected to another power supply. Foot massager 52 or footrest 50, separately or in combination, are placed on exterior floor mat 24 in front of seating system 14 just outside front flaps 30 of exterior housing 18. Foot massager 52 or footrest 50, separately or in combination, are placed outside of housing 12 to allow for adjustment of leg position, to reduce noise sensed by user 70 from foot massager 52 if that is being used and to lessen feelings of claustrophobia.

Scent diffuser 58 is equipped with scent (e.g., oil) and placed on interior floor mats 22 at an appropriate location inside exterior housing 18. In one embodiment, such an appropriate location would be in a front corner inside exterior housing 18; other locations are possible but should be located away from seating system 14.

Audio player 54 is connected to headphones 56. Other items, including eye mask 60, footrest 50, as well as earpiece covers 64 and foot covers 62 are organized and placed within easy access of user 70 or attendant.

Figure 9:
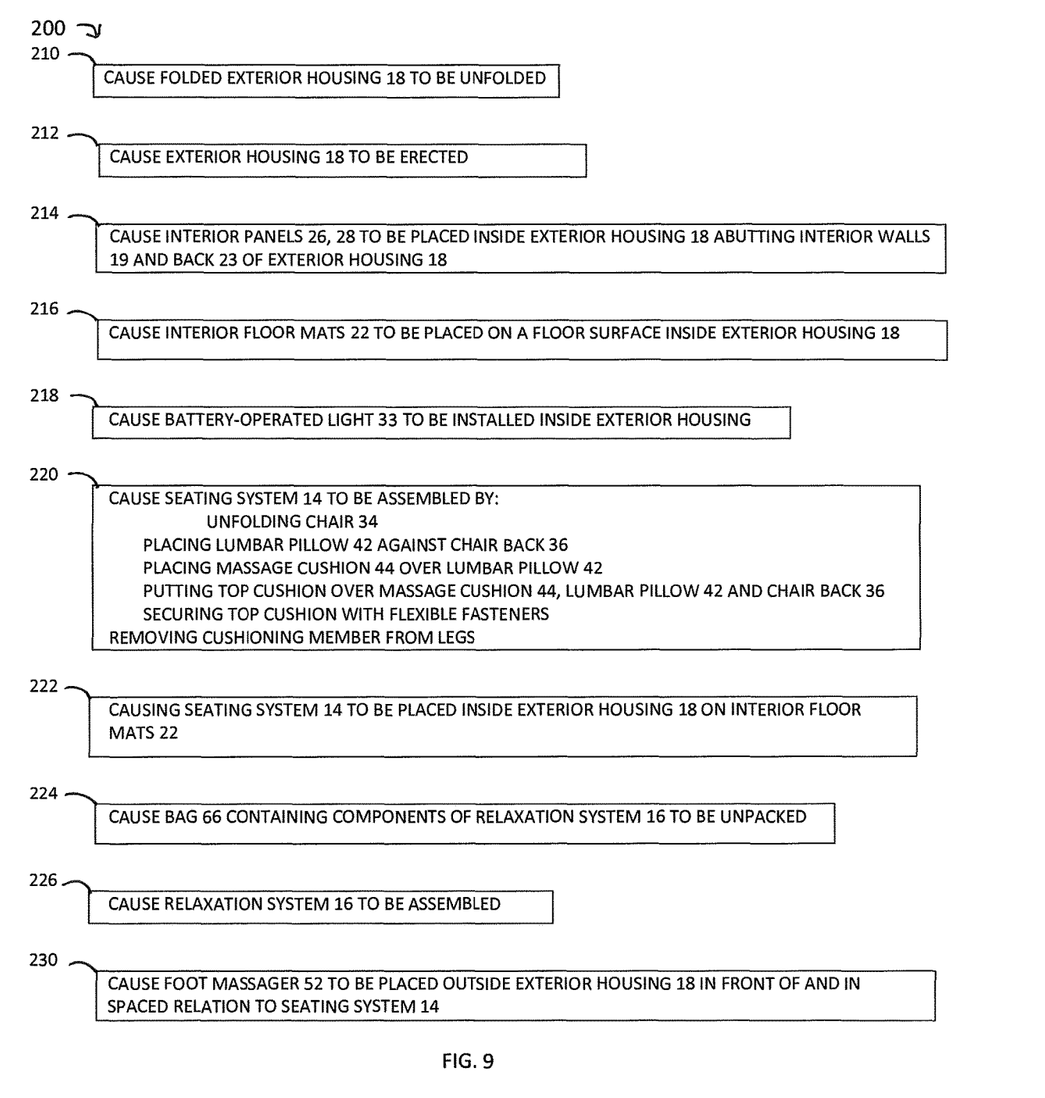
FIG. 9 illustrates steps in another embodiment of a method of the present invention for assembling the relaxation pod.

Another embodiment of method 200 comprises steps for assembling relaxation pod 10 in which seating system 14 has not been fully assembled and is assembled on-site. FIG. 9.

At the outset, folded exterior housing 18 and interior panels 26, 28, folded seat assembly 14 and the remaining components (e.g., relaxation system 16 components and floor mats 22, 24) packed in bag 66 are transported to a desired location to assemble relaxation pod 10.

Folded exterior housing 18 containing interior panels 26, 28 is unfolded 210 and unzipped. Exterior housing 18 is stood up 212. Interior panels 26, 28 are placed 214 inside exterior housing abutting interior walls 19 and back 23 of exterior housing 18. Bag 66 containing components of relaxation system 16, as well as floor mats 22, 24, is unpacked 224. Interior floor mats 22 are unrolled and placed 216 inside exterior housing 18 to cover the floor of exterior housing 18, although this is not required. Exterior floor mat 24 is unrolled and placed outside of exterior housing, making housing 12.

In the embodiments shown, light 33 is inflated and installed 218 in exterior housing 18 by attaching it attached to ceiling 32 of exterior housing 18. In one embodiment, this is done using hook-and-loop closures, although other means are possible. Then light 33 is turned on.

At step 220, folded seating system 14 is assembled in the manner previously described. Chair 34 is unfolded 220 and cushioning member 68 is removed from leg 38(*s*) 220. Lumbar pillow 42 is placed 220 against back 36 of chair 34 just above seat 39 and secured, such as with straps 48. Massage cushion 44 is placed 220 over lumbar cushion 42. Chair cover 46 is then placed over back 36, seat, 39 and arms 40. Top cushion 45 is placed 220 over back 36, lumbar pillow 42, massage cushion 44 and chair cover 46. Top cushion 45 is secured 220 to chair 34 with flexible fasteners (e.g., straps 48). Neck pillow 49 is then placed on chair 34 making seating system 14.

Assembled seating system 14 is placed 222 inside exterior housing 18 on interior floor mats 22. Massage cushion 44 is plugged in to or otherwise connected to an electrical outlet or other power supply. Exterior floor mat 24 is placed outside of exterior housing 18 and foot massager 52 is placed on exterior floor mat 24 in front of seating system 14.

Foot massager 52 or footrest 50, separately or in combination, is placed 230 outside of exterior housing 18, 18 to allow for adjustment of leg position, to reduce noise sensed by user 70 from foot massager 52 if that is being used and to lessen feelings of claustrophobia.

At step 226, relaxation system 16 is assembled. Scent diffuser 58 is equipped with scent (e.g., oil) and placed on interior floor mats 22 at an appropriate location inside exterior housing 18. In one embodiment, such an appropriate location would be in a front corner inside exterior housing 18; other locations are possible but preferably should be located away from seating system 14.

Audio player 54 is connected to headphones 56. Other items, including eye mask 60, footrest 50, as well as earpiece covers 64 and foot covers 62 are organized and placed within easy access of user 70 or attendant.

Figure 10:
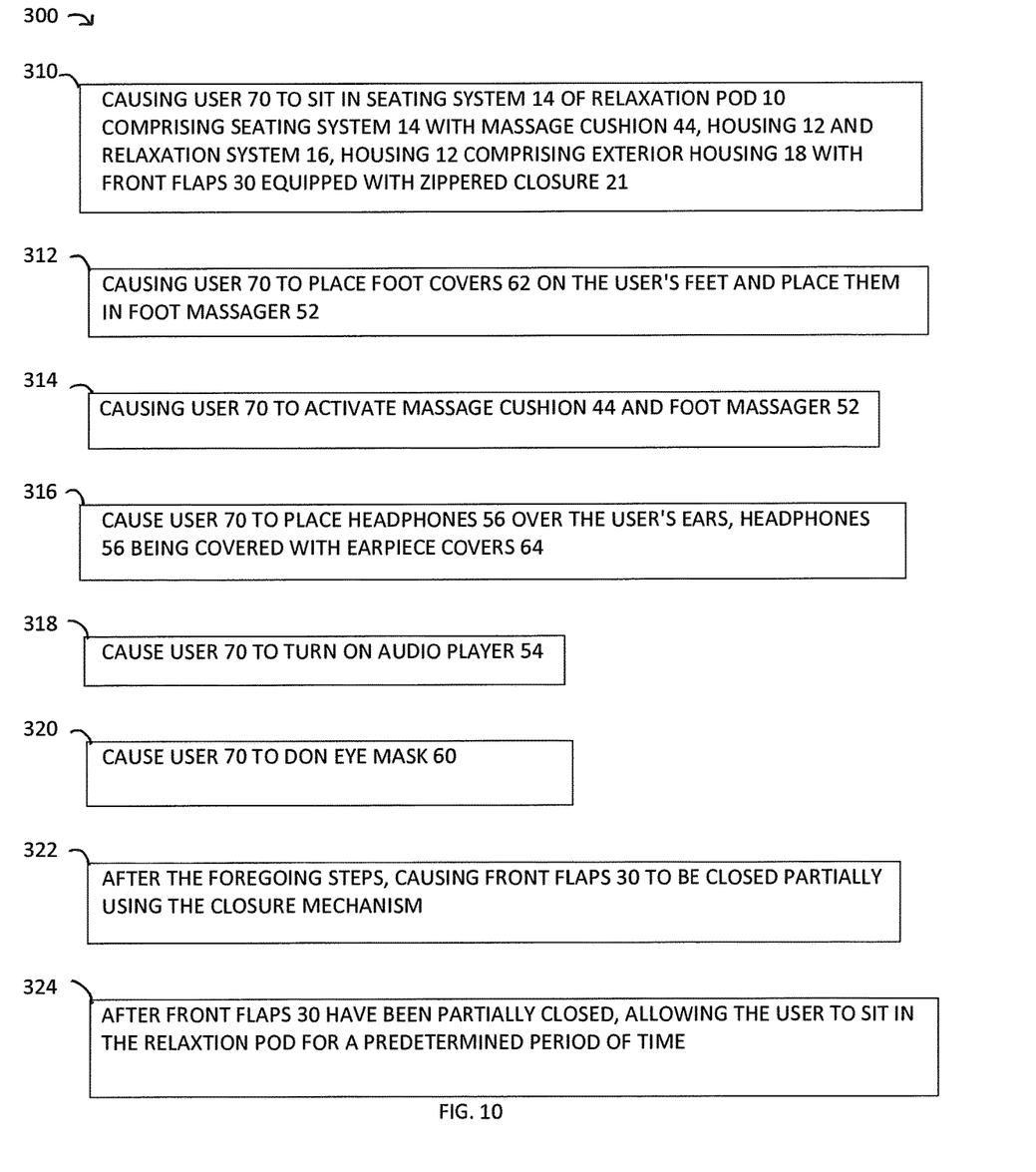
FIG. 10 illustrates steps in an embodiment of a method of the present invention for using the relaxation pod.

An embodiment of method 300 for using relaxation pod will now be described with reference to FIGS. 6, 7 and 10. User 70 approaches relaxation pod 10, is caused to sit 310 in chair 34 of seating system 14 and is instructed to remove shoes 71 and place them outside exterior housing 18, which user 70 does.

Foot massager 52 or footrest 50, separately or in combination, is placed outside of housing 12 to allow for adjustment of leg position, to reduce noise sensed by user 70 from foot massager 52 if that is being used and to lessen feelings of claustrophobia. To use these devices, user 70 is provided with foot covers 62 which are placed 312 on user's 70 feet. User 70 is then caused to place 312 her feet in foot massager 52 or on footrest 50. Chair 34 of seating system 14 is then adjusted to the user's 70 desired degree of recline and neck pillow 49 is adjusted for user 70. Massage cushion 44 is activated 314 and the desired features for vibration and/or heat are selected; foot massager 52 is also activated. User 70 sits down in seating system 14. FIG. 6.

Earpiece covers 64 are placed over headphones 56 and headphones 56 are placed 316 over user's 70 ears. FIG. 6. Audio player 54 is turned on 318 and appropriate adjustments are made for volume. In another embodiment, selection may also be made for a meditation track.

Eye mask 60 is placed 320 over user's 70 eyes. In one embodiment in which a disposable surgical mask is used, eye mask 60 is pinched over the bridge of the nose to reduce light penetration. FIG. 6.

After the foregoing steps, the front flaps 30 are closed 322 partially using the closure mechanism (e.g., zippered closure 21). In an embodiment, zip cord 20 is pulled, causing zippered closure 21 to close front flaps 30 to the user's 70 knees. FIG. 7.

The meditation session begins and continues for a predetermined period of time, which may be the period of time in which it takes to play the selected meditation track. Any other length of time may also be selected.

When the session is completed, the closure mechanism (e.g., zippered closure 21) is used to open front flaps 30. In the embodiment shown, zippered enclosure 21 is opened using zip cord 20. User 70 exits.

Before the next user 70 enters relaxation pod 10, all surfaces with which user 70 or the attendant, if any, has had any physical contact are wiped down with sanitizing wipes or other type of disinfectant, including top cushion 45, chair cover 46, headphones 56, audio player 54, foot massager 52, control for massage cushion 44. Used earpiece covers 64, foot covers 62 and eye mask 60 are discarded. New earpiece covers 64 are placed on headphones 56. New foot covers 62 and eye mask 60 are readied for the next user 70.

As would be familiar to one of ordinary skill in the art after becoming familiar with the teachings of the invention, many of these method steps may be performed in any sequence.

By using relaxation pod 10 of the present invention according to embodiments of method 300 in this manner, user 70 can experience a multi-sensory relaxation period in a self-contained "pop-up" fully-portable relaxation pod 10 in a reduced-noise environment without having to be touched by another person. Causing the user's 70 feet to be outside exterior housing 18 in foot massager 52 subjects the user to less noise (which is also aided by noise-cancelling headphones 56), as well as lessening feelings of claustrophobia that might arise from having the user 70 fully enclosed inside housing 12 during a meditation session. FIGS. 6, 7.

In understanding the scope of the present invention, the term "comprising" and its derivatives, as used herein, are intended to be open ended terms that specify the presence of the stated features, elements, components, groups, and/or steps, but do not exclude the presence of other unstated features, elements, components, groups, and/or steps. The foregoing also applies to words having similar meanings such as the terms, "including," "having" and their derivatives. Any terms of degree such as "substantially," "about" and "approximate" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adapted to another embodiment. It should be noted that while the present invention is shown and described herein as it could be used in conjunction with a configuration of various components, it could be utilized with other configurations, either now known in the art or that may be developed in the future, so long as the objects and features of the invention are achieved, as would become apparent to persons having ordinary skill in the art after having become familiar with the teachings provided herein. Consequently, the present invention should not be regarded as limited to that shown and described herein. It is not necessary for all advantages to be present in a particular embodiment at the same time. Thus, the foregoing descriptions of the embodiments according to the present invention are provided for illustration only, and not for the purpose of limiting the invention as defined by the appended claims and their equivalents.

Having herein set forth preferred embodiments of the present invention, it is anticipated that suitable modifications can be made thereto which will nonetheless remain within the scope of the invention, including all changes that come within the meaning and range of equivalents. The invention shall therefore only be construed in accordance with the following claims:

What is claimed is:

1. A portable relaxation pod, comprising:
a portable housing, the portable housing being foldable and comprising an exterior housing with walls, front flaps, an interior ceiling and interior panels abutting the interior ceiling and an interior surface of the walls, the interior panels each comprising an acoustic foam layer and a corrugated plastic layer, the front flaps being configured to close part way to accommodate a user;
a portable seating system, the seating system being placed inside the exterior housing and comprising a foldable chair equipped with a massage cushion placed against a back surface and seat of the foldable chair; and
a relaxation system, the relaxation system comprising an eye mask, headphones connected to an audio player and a portable foot massager located outside of the housing.

2. The portable relaxation pod of claim 1, further comprising:
a carrying system, the carrying system comprising a carrier and a cushioning member attached to at least one leg of the chair.

3. The portable relaxation pod of claim 2, wherein the carrying system comprises the portable housing folded to contain the interior panels and the foldable chair being folded together with the massage cushion.

4. The portable relaxation pod of claim 3, wherein the foldable chair comprises a lumbar pillow placed between the back surface and the massage cushion and a cover placed over at least the massage cushion, back surface and seat, the cover being secured with at least one flexible fastener, and the foldable chair being folded together with the massage cushion, lumbar pillow and cover.

5. The portable relaxation pod of claim 2, wherein the carrier is configured to contain the components of the relaxation system.

6. The portable relaxation pod of claim 1 wherein the interior panels are configured to stand substantially upright within the exterior housing without being secured to the interior surface.

7. The portable relaxation pod of claim 1 wherein the portable housing comprises a light, the light being battery-operated and configured to be attached to the interior ceiling or the interior surface of the walls of the portable housing.

8. The portable relaxation pod of claim 1, wherein the portable housing comprises an interior floor mat sized to fit within the portable housing.

9. The portable relaxation pod of claim 1, wherein the front flaps comprise a closure mechanism configured to permit the front flaps to be closed at least partially.

10. The portable relaxation pod of claim 9, wherein the closure mechanism comprises a zippered closure.

11. A method for assembling a portable relaxation pod comprising a folded seating system, a relaxation system packed in a carrier and a folded housing,
the folded seating system comprising a folding chair, a lumbar pillow, a massage cushion and a too chair cover with flexible fasteners,
the relaxation system comprising a foot massager, audio player and headphones,
the housing including an interior floor mat, a light, interior panels and a foldable exterior housing comprising a back surface, front flaps and wads, the method comprising the steps of:
causing the folded housing, packed relaxation system and folded seating system to be transported to a selected location;
causing the exterior housing to be unfolded at the selected location;
causing the exterior housing to be erected;
causing the interior panels to be placed inside the exterior housing so that the interior panels abut the walls and the back surface;
causing the interior floor mat to be placed inside the exterior housing;
causing the light to be placed inside the exterior housing;
causing the seating system to be assembled by:
causing the chair to be unfolded;
causing the lumbar pillow to be placed against a back of the folding chair;
causing the top chair cover to be placed over the chair back, lumbar pillow and massage cushion;
causing the top cushion to be secured with flexible fasteners; causing the assembled seating system to be placed inside exterior housing on the interior floor mat behind the front flaps;
causing the carrier to be unpacked; and
causing the foot massager to be placed outside of the exterior housing and substantially in front of the seating system.

12. The method of claim 11, wherein the housing comprises an exterior floor mat, further comprising causing the exterior floor mat to be placed outside of the exterior housing substantially in front of the front flaps.

13. The method of claim 11, wherein the relaxation system comprises a footrest, further comprising causing the footrest to be placed outside of the exterior housing.

14. The method of claim 11, wherein the relaxation system comprises a scent diffuser, further comprising causing the scent diffuser to be placed outside of the exterior housing.

15. A method for using a portable relaxation pod comprising a relaxation system including headphones, an audio player, a foot massager and an eye mask, a seating system having a massage cushion and a housing having an exterior housing with front flaps including a closure mechanism, comprising:
causing a user to sit in the seating system located inside the housing;
causing the user to place the user's feet in a foot massager device located outside of the housing;
causing the massage cushion to be activated;
causing the foot massager to be activated;
causing the user to don the eye mask;
causing the headphones to be placed over the user's ears;
causing the audio player to be activated;
causing the front flaps to be closed partially using the closure mechanism; and
after causing the front flaps to be partially closed, permitting the user to sit in the relaxation pod for a predetermined period of time.

16. The method of claim 15, wherein causing the front flaps to be partially closed comprises causing the front flaps to be closed to a position just above the user's knees.

17. The method of claim 15, wherein the relaxation system comprises a scent diffuser and further comprising:

causing the scent diffuser to be placed outside the exterior housing; and
causing the scent diffuser to be activated.

* * * * *